(12) United States Patent
Suárez et al.

(10) Patent No.: US 7,432,401 B2
(45) Date of Patent: Oct. 7, 2008

(54) METHOD FOR THE PREPARATION OF 1,5-BIS(4-HYDROXY-3-METOXY-PHENYL)-PENTA-1,4-DIEN-3-ONE AND DERIVATIVES WITH ANTITUMORAL PROPERTIES

(75) Inventors: José Agustin Quincoces Suárez, São Paulo (BR); Klaus Peseke, Elmenhors Lichtenhagen (DE); Markus Kordian, Rostock (DE); João Ernesto Carvalho, Campinas (BR); Luciana Konecny Kohn, Campinas (BR); Márcia Aparecida Antônio, Paulinia (BR); Heloiza Brunhari, Guarulhos (BR)

(73) Assignee: Fundação de Amparo a Pesquisa Do Estado de São Paulo, São Paulo (BR)

( * ) Notice: Subject to any disclaimer, the term of this patent is extended or adjusted under 35 U.S.C. 154(b) by 0 days.

(21) Appl. No.: 10/536,667

(22) PCT Filed: Nov. 28, 2003

(86) PCT No.: PCT/BR03/00177

§ 371 (c)(1),
(2), (4) Date: Dec. 28, 2005

(87) PCT Pub. No.: WO2004/047716

PCT Pub. Date: Jun. 10, 2004

(65) Prior Publication Data

US 2006/0128997 A1  Jun. 15, 2006

(30) Foreign Application Priority Data

Nov. 28, 2002 (BR) .................................. 0207141

(51) Int. Cl.
*C07C 45/72* (2006.01)
*A61K 31/12* (2006.01)

(52) U.S. Cl. ........................ 568/313; 514/678; 514/679
(58) Field of Classification Search ................ 568/313; 514/678, 679
See application file for complete search history.

(56) References Cited

U.S. PATENT DOCUMENTS 4,521,629 A * 6/1985 Cortese et al. .............. 568/313

OTHER PUBLICATIONS

Sardjiman et al. European Journal of Medicinal Chemistry, 1997, vol. 32, p. 625-630.*
Artico et al. Journal of Medicinal Chemistry, 1998, vol. 41, p. 3948-3960.*

* cited by examiner

*Primary Examiner*—Sikarl A Witherspoon
(74) *Attorney, Agent, or Firm*—TraskBritt, P.C.

(57) ABSTRACT

This patent of invention reports the method for the preparation of 1,5-bis(4-hydroxy-3-methoxyphenyl)-penta-1,4-dien-3-one and derivatives with antitumoral properties: the sample denominated 37 compound was obtained with high yield and purity with ultrasonic technique presenting cytostatic activity (growth inhibition) in the concentrations evaluated and cytotoxic activity (cellular death) from the concentration of 0.25 mg/mL against nine different types of human cancer cell lines. This compound has a $LD_{50}$, equals to 8.54 g/Kg. That means this product can be considered itself as practically nontoxic. Doxorubicin, anticarcinogen medicine used as reference in all these tests, is a product extremely toxic ($LD_{50}$ of 20 mg/Kg) and it does not inhibit the growth of Mama NCI-ADR cell line (the one that expresses the phenotype of resistance against multiple drugs), therefore, out product presented a strong cytostatic activity. Other derivatives also presented a strong cytostatic activity, especially the one denominated EHB1 compound.

22 Claims, 10 Drawing Sheets

| Compound | Human Cell Lines tested ED$_{50}$ (µg/mL) | | | | | | | | |
|---|---|---|---|---|---|---|---|---|---|
| | UACC-62 | MC-7 | NCI-ADR | 786-O | NCI-460 | K-562 | PC-03 | OVCAR-03 | HT29 |
| 37 | 0.03 | 0.04 | 0.27 | 0.65 | 0.5 | 0.6 | 0.41 | 0.72 | 0.75 |
| EHB1 | 1.77 | 0.45 | 1.28 | 0.27 | 0.7 | 0.58 | 0.39 | 0.57 | 0.61 |
| HB6 | 14.16 | 8.43 | 3.34 | 3.64 | 15.8 | 2.22 | 27.99 | 14 | 1.87 |
| HBM1 | 0.75 | 0.71 | 0.84 | 1.19 | 0.66 | 0.65 | 0.82 | 0.82 | 0.86 |
| HB5 | 1.25 | 1.96 | 1.11 | 2.67 | 2.58 | 2.84 | 1.59 | 43 | 1.26 |

*FIG. 1*

| Name of the compound | HT-1080 | Colon L5-26 |
|---|---|---|
| 1  3-hydroxy-2,2-dimethyl-8-prenylchromane-6-propenoic acid | 71.53 | 77.07 |
| 2 2,2-dimethyl-8-prenyl-2H-1-benzopyran-6-yl-2-propenoic acid | 46.86 | 50.22 |
| 3  3,5-diprenyl-4-hydroxycinnamic acid | 45.47 | 59.32 |
| -dihydrocinnamoyloxy-3-prenylcinnamic acid | 25.94 | 77.90 |

*FIG. 2*

| Animal | Initial Weight (g) | Administered Volume (ml) | Final Weight (g) | Deaths (n) |
|---|---|---|---|---|
| 1 | 24.5 | 0.25 | 26.4 | 0 |
| 2 | 25.4 | 0.25 | 28.0 | 0 |
| 3 | 25.4 | 0.25 | 28.6 | 0 |
| 4 | 24.1 | 0.24 | 27.4 | 0 |
| 5 | 26.6 | 0.27 | 29.0 | 0 |
| 6 | 24.8 | 0.25 | 27.8 | 0 |
| 7 | 22.5 | 0.23 | 25.0 | 0 |
| 8 | 29.7 | 0.30 | 31.2 | 0 |
| 9 | 22.4 | 0.22 | 25.4 | 0 |
| 10 | 20.6 | 0.21 | 22.8 | 0 |

Average ± dpm:  24.60 ± 2.51     Average ± dpm:  27.88 ± 1.02

| Animal | Initial Weight (g) | Administrated Volume (ml) | Final Weight (g) | Deaths (n) |
|---|---|---|---|---|
| 1 | 28.3 | 0.28 | 30.3 | 0 |
| 2 | 30.9 | 0.31 | 32.5 | 0 |
| 3 | 24.6 | 0.25 | 25.9 | 0 |
| 4 | 25.4 | 0.25 | 28.0 | 0 |
| 5 | 25.1 | 0.25 | 27.9 | 0 |
| 6 | 23.2 | 0.23 | 25.6 | 0 |
| 7 | 23.6 | 0.24 | 26.0 | 0 |
| 8 | 23.6 | 0.24 | 25.8 | 0 |
| 9 | 26.0 | 0.26 | 28.3 | 0 |
| 10 | 24.0 | 0.24 | Death | 1 |

Average ± dpm: 25.47 ± 2.43    Average ± dpm: 27.81 ± 2.35

| Animal | Initial Weight (g) | Administrated Volume (ml) | Final Weight (g) | Deaths (n) |
|---|---|---|---|---|
| 1 | 29.8 | 0.30 | 32.5 | 0 |
| 2 | 25.5 | 0.26 | 26.9 | 0 |
| 3 | 33.2 | 0.33 | 35.9 | 0 |
| 4 | 25.9 | 0.26 | 28.9 | 0 |
| 5 | 26.3 | 0.26 | 29.0 | 0 |
| 6 | 28.9 | 0.29 | 30.2 | 0 |
| 7 | 26.7 | 0.27 | 28.0 | 0 |
| 8 | 23.3 | 0.23 | 25.9 | 0 |
| 9 | 21.2 | 0.21 | 23.5 | 0 |
| 10 | 23.3 | 0.23 | Death | 1 |

Average ± dpm:  26.41 ± 3.52     Average ± dpm:  28.98 ± 3.65

| Animal | Initial Weight (g) | Administrated Volume (ml) | Final Weight (g) | Deaths (n) |
|---|---|---|---|---|
| 1 | 24.9 | 0.25 | 25.9 | 0 |
| 2 | 21.0 | 0.21 | 24.0 | 0 |
| 3 | 25.4 | 0.25 | 27.8 | 0 |
| 4 | 22.2 | 0.22 | 25.6 | 0 |
| 5 | 24.0 | 0.24 | 27.0 | 0 |
| 6 | 23.8 | 0.24 | 25.8 | 0 |
| 7 | 22.5 | 0.23 | 24.9 | 0 |
| 8 | 23.5 | 0.24 | 25.9 | 0 |
| 9 | 24.2 | 0.24 | Death | 1 |
| 10 | 25.3 | 0.25 | Death | 1 |
| Average ± dpm: | 23.68 ± 1.42 | Average ± dpm: | 25.86 ± 1.17 | |

| Cell Line | Code |
|---|---|
| Lung | *NCI460* |
| Mamma | MCF-7 |
| | NCI ADR* |
| Melanoma | UACC-62 |
| Colon | HT 29 |
| Renal | 786-0 |
| Ovary | OVCAR-3 |
| Prostate | *PC-3* |
| Leukemia | *K-562* |

*FIG. 18*

METHOD FOR THE PREPARATION OF 1,5-BIS(4-HYDROXY-3-METOXY-PHENYL)-PENTA-1,4-DIEN-3-ONE AND DERIVATIVES WITH ANTITUMORAL PROPERTIES

TECHNICAL FIELD

The present patent of invention refers to a NEW METHOD FOR THE PREPARATION OF 1,5-BIS(4-HYDROXY-3-METHOXYPHENYL)-PENTA-1,4-DIEN-3-ONE AND DERIVATIVES WITH ANTITUMORAL ACTIVITIES.

BACKGROUND

Bibliographical background about 1,5-bis(4-hydroxy-3-methoxyphenyl)-penta-1,4-dien-3-one compound and derivatives and its method for the preparation.

The compound denominated 1,5-bis(4-hydroxy-3-methoxyphenyl)-penta-1,4-dien-3-one is known since the year 1927 since E. Glaser and E. Tramer for the first time reported its synthesis with a 60% yield (Journal für praktische Chemie, 116, 331-346, 1927) from the vanillin and acetone in the presence of concentrated hydrochloric acid, used as a catalyzer.

Further, P. Ramanan and M. Rao synthesized this product in 1989 (Indian Journal Pharm. Sci., 51, 207, 1989) from 4-O-methoxymethylvanillin and acetone in an alkaline medium, obtaining a yield of 42% after purifying the same using the thin-layer chromatograph (silica gel).

In 1997, a group integrated by S. Sardjiman, et al. (Eur. Journal Med. Chem. 32, 625-630, 1997) developed a new variant synthesis using equimolecular quantities of vanillin and acetone in the presence of concentrated hydrochloric acid, reporting a raw yield of 89% (without purifying). For this reason, the melting point indicated in this procedure was 58° C. less than the one reported by Glaser and Tramer.

M. Artico et al. also obtained this substance one year later (Journal Med. Chem. 41, 3948-3960, 1998) only obtaining a poor yield of 18%. The melting temperature (114-116° C.) is lower than the one reported by Glaser and Tramer, what is makes think that the compound was not obtained pure in despite of the use of the chromatograph of column.

Additionally, we can find in the bibliographic revision the article of the American patent (U.S. Pat. No. 4,521,629 of Jun. 4, 1985) of N. Cortese et al. entitled: "Method for the preparation of 1,5-bis-aryl-1,4-pentadien-3-ones." This invention reports to a method of preparing certain bis-arylpentadienones containing fluorine, that were used as intermediate compounds for the preparation of insecticidal substituted amidinohydrazones, but it does not protect the products that appear in our patent request.

Furthermore, the following documents of other patents related to this family of organic compounds were found:

1-"Hair tonics containing bis(hydroxyphenyl)pentadienones." Authors of the patent: Morita, Kazuyoshi; Hamada, Kazuto. Company: Kanebo, Ltd, Japan. Country: Jpn. Kokai Tokyo Koho, 7 pp. Idiom: Japanese. CA-Number: 134:183278. PI: JP 2001048756, A2 20010220 JP 1999-224982 19990809.

2-"Skin-lightening cosmetics containing distyryl ketones." Author: Morita, Kazuyoshi. Company: Kanebo, Ltd., Japan. Country: Jpn. Kokai Tokyo Koho, 7 pp. Idiom: Japanese. CA-Number: 131:149078. PI: JP 11209235 A2 19990803 JP 1998-10414 19980122.

3-"Acidic planting baths and methods for electrodepositing bright and ductile zinc-nickel allows and additive composition for these baths." Company: McGean-Rohco, Inc., USA. Author: Canaris, Valerie M. Country: U.S., 8 pp. Idiom: English. CA-Number: 111:183131. PI: US 4832802 A 19890523 US 1988-206017 19880610 EP 346161 A1 19891213 EP 1989-305925 19890612.

4-"Photopolymerizable compositions." Compound: Eastman Kodak Co., USA. Authors: Noonan, John M.; McConkey, Robert C.; Arcesi, J. A.; Rauner: Frederick J. Country: Brit., 19 pp. Idiom: English PI: GB 1425476 A 19760218 GB 1973-3986 19730322 US 3748133 A 19730724 US 1972-237929 19720324.

None of these four patents, either directly or indirectly, are related to the antiproliferate properties shown by 1,5-bits(4-hydroxy-3-methoxyphenyl)-penta-1,4-dien-3-one and its derivatives.

Taking into account the bibliographic revision performed by the company Bypropind Patents and Trademarks based on the tracking in the Chemical Abstracts collection, of Lifescience, of Biomed of Fiocruz library and by us in the Beilstein collection, we have concluded the there is no patent of that compound and its derivatives applicable in the cancer treatment or even the ultrasonic technique in despite of the compound has been synthesized in the year of 1927 and so that the patent request is possible and legitimate.

SUMMARY OF THE INVENTION

The present patent of invention reports the antitumoral properties of 1,5-bis(4-hydroxy-3-methoxyphenyl)-penta-1,4-dien-3-one and derivatives and its procedure of preparing.

The sample denominated 37/01 compound was obtained with high yield and purity by the ultrasonic technique presenting cytostatic activity (growth inhibition) in the concentrations evaluated and killed cell activity (cellular death) from the concentration of 0.25 µg/mL against nine different types of human cancer. This compound has a $LD_{50}$, equals to 8.54 g/Kg. That means this product can be considered itself as practically nontoxic. Doxorubicin, anticarcinogen medicine used as reference in all of these tests, is a product extremely toxic ($LD_{50}$ of 20 mg/Kg) and its does not inhibit the growth of the Mama NCI-ADR cell lines (the one that expresses the phenotype of resistance against multiple drugs), therefore our product presented a strong cytostatic activity.

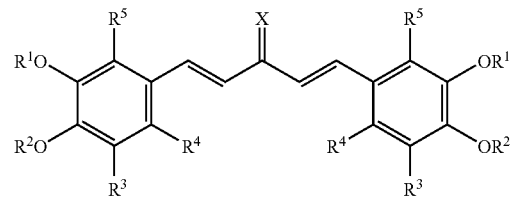

37: $R^1$-$CH_3$; $R^2$-H; $R^3$-H; $R^4$-H; $R^5$=H; X-O
EHB1: $R^1$=$CH_3$; $R^2$=$H_3CCO$; $R^3$=H; $R^4$=H; $R^5$=H; X=O
HB6: $R^1$=$CH_3$; $R^2$=$CH_2CH$=$C(CH_3)_2$; $R^3$=H; $R^4$=H; $R^5$-H; X-O
HBM1: $R^1$=$CH_3$; $R^2$=$CH_3$; $R^3$=H; $R^4$=H; $R^5$=H; X=O
HB5: $R^1$=$CH_3$; $R^2$=H; $R^3$=H; $R^4$=H; $R^5$=H; X=C(CN)$_2$
HB10: $R^1$=$CH_3$; $R^2$=H; $R^3$=$CH_2CH$=$C(CH_3)_2$; $R^4$=H; $R^5$=H; X=O
HB11: $R^1$=$CH_3$; $R^2$=H; $R^3$=H; $R^4$=H; $R^5$=H; X=C(CN)$CO_2C_2H_5$
HB12: $R^1$=H; $R^2$=H; $R^3$=H; $R^4$=H; $R^5$=H; X=O
HB13: $R^1$=$CH_3$; $R^2$=H; $R^3$=Br; $R^4$=H; $R^5$=H; X=O

HB14:$R^1$=$CH_3$; $R^2$=$CH_2CH$=$C(CH_3)_2$; $R^3$=Br; $R^4$=H; $R^5$-H; X=O

HB15:$R^1$=H; $R^2$=H; $R^3$=$CH_2CH$=$C(CH_3)_2$; $R^4$=$CH_2CH$=$C(CH_3)_2$; $R^5$=H; X=O

Antitumoral activity shown by synthesized compounds is shown in FIG. 1.

The following designations are utilized in FIG. 1: Legend: NCI460 (Lung tumor): UACC62 (Melanoma); MCF7 (Normal mamma tumor); NCIADR (Mamma tumor which expresses the phenotype resistance against multiple drugs) HT29 (Colon tumor); 786-O (Renal tumor); OVCAR-3 (Ovary tumor); PC-3 (Prostate tumor); K-562 (Leukemia); $ED_{50}$ (effective doses 50 expressed in micrograms by milliliters µg/mL).

Remarks:

All these results can be considered excellent, if we take into reference the ones published in the literature:

Banskota AH, et al. Chemical Constituents of Brazilian Propolis and their cytotoxic activities: J. Nat. Prod. 61, 896-900, 1998.

Banskota A H, et al. Two Novel Cytotoxic Benzofuran Derivatives from Brazilian propolis; J. Nat Prod. 63, 1277-1279, 2000

Kimoto T, et al. Apoptosis and Suppression of tumor growth by Artepillin C extracted from Brazilian Propolis; Cancer Detect, Prev. 22(6), 505-15, 1998.

It is observed that most of our products presented a strong antiproliferate action in concentration ranges (in ppm) much lower than the ones shown by some of the isolated compounds of the Brazilian Propolis.

Cytotoxicity of some isolated compounds of Brazilian Propolis by Banskota and Kimoto are shown in FIG. 2.

We want to point out that the obtained products by our team consist of raw material of our research project, from which we are obtaining new derivatives, guided by the principle of analogy and the results of TOPS-MODE predictions.

Curves Concentration response of the tested compounds is shown in FIG. 3.

BRIEF DESCRIPTION OF THE DRAWINGS

FIG. 1 is a table of data of antitumoral activity shown by synthesized compounds.

FIG. 2 is a table of data concerning the cytotoxicity of some isolated compounds of Brazilian Propolis by Banskota and Kimoto.

FIG. 18 is a table of cell lines used in the assessment assays.

DETAILED DESCRIPTION OF THE INVENTION 37 compound, obtained by means of an organic synthesis procedure, presented cytostatic activity (growth inhibition) for all cell lines and cytotoxic activity (cellular death) for NCI460 (Lung), UACC62 (Melanoma) and MCF7 (Mamma) and NCIADR (Mamma resistant) from 0.25 µg/mL in the first antitumoral tests performed into CPQBA, IJNICAMP, Sep. 24, 2001.

Figure 3:
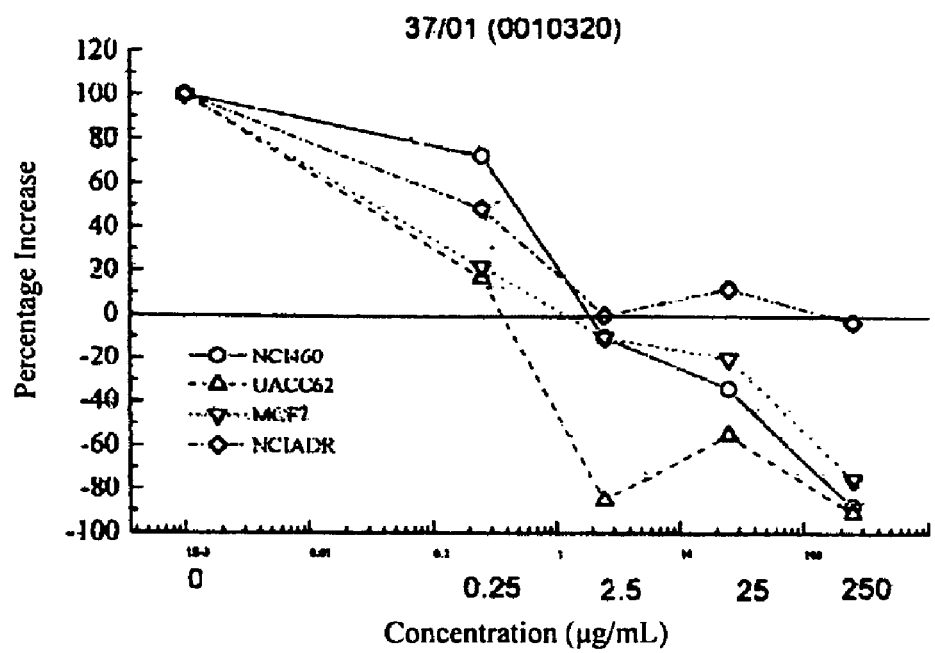
FIG. 3 is a graph plotting percentage of growth versus concentration of the antitumoral activity of the synthesized compounds in FIG. 1.
Figure 4:
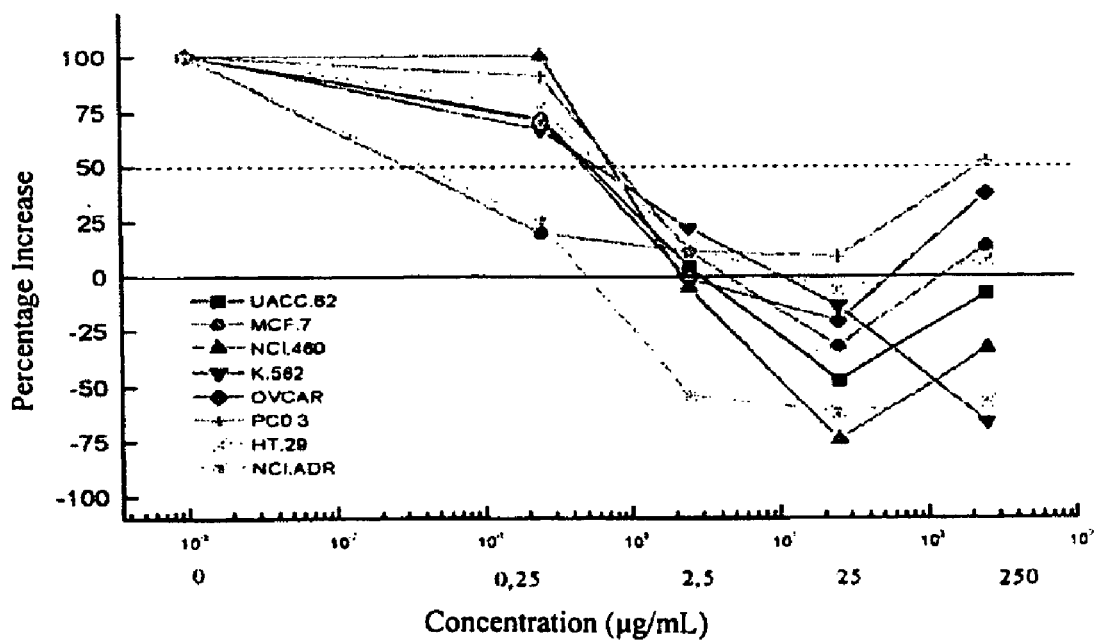
FIG. 4 is a graph plotting percentage of growth versus concentration for the antiproliferative activity of compound 37 or HB1.

Later, these tests of antiproliferate activity were extended to the following cell liens:

Colon: Renal; Ovary; Prostate; Leukemia. A graph showing the results of these tests using compound 37 is shown in FIG. 4.

Curve Concentration response of 37.

Figure 5:
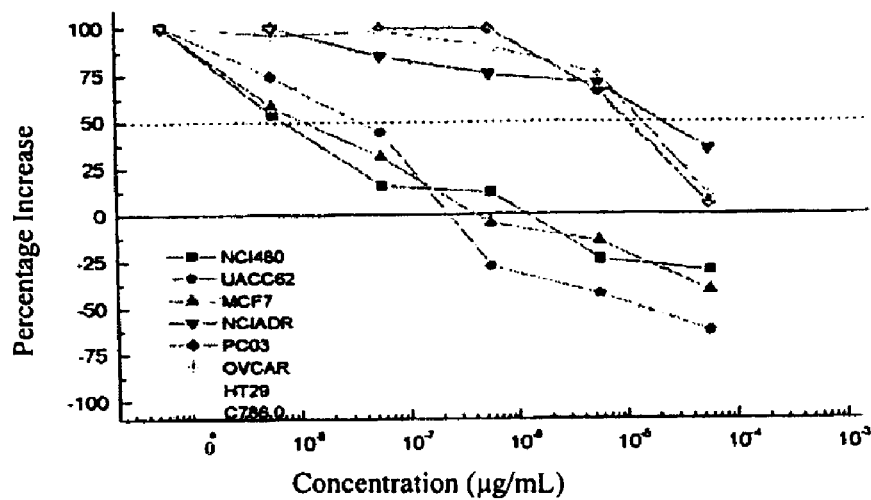
FIG. 5 is a graph plotting percentage of growth versus concentration for the response of Doxorubicin.

The results of this compound were compared with Doxorubicin (commercial anticarcinogen used as a standard in these tests) being so similar and in some cases higher than this commercial anticarcinogen. A graph showing these results is shown in FIG. 5.

Curve concentration response Doxorubicin.

For example, our product inhibited the growth of the Mama NCI-ADR cell line (the one that presents the phenotype of resistance against multiple drugs). This result becomes itself very interesting since Doxorubicin, utilized as a positive control, did not inhibit the growth of this human cell line.

Figure 6:
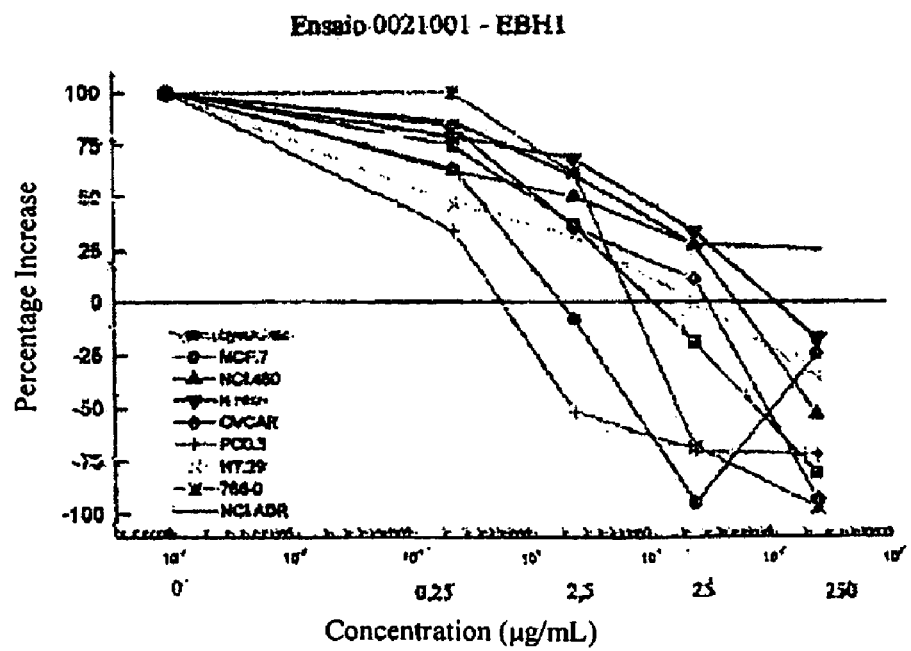
FIG. 6 is a graph of the antitumoral activity of 1,5-bis(4-hydroxy-3-methoxyphenyl)-penta-1-4-dien-3-one.

The derivatives of 1,5-bis(4-hydroxy-3-methoxyphenyl)-penta-1,4-dien-3-one shows the antitumoral activity identified in FIG. 6:

The sample denominated EHBI compound presented cytostatic activity for all cell lines from the concentration of 0.25 µg/mL and cytotoxic activity from the concentration of 25 µg/mL, excepting NCI-ADR cell line which had only its growth inhibition around 25%. The results showed this sample was not selective for the studied cell lines.

Figure 7:
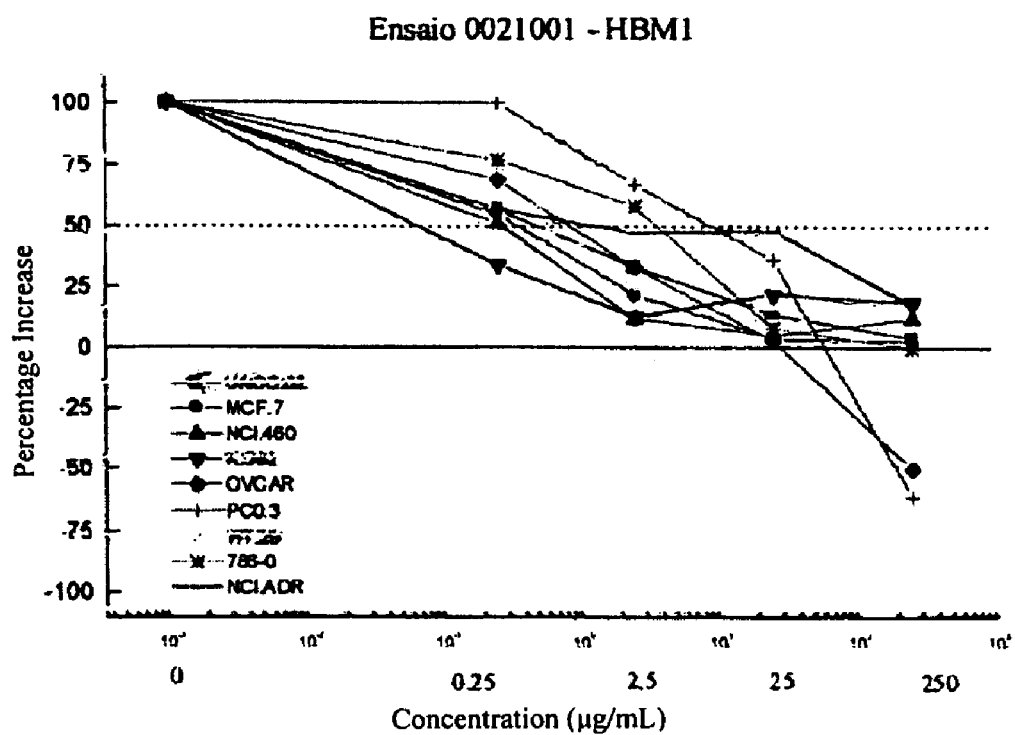
FIG. 7 is a graph plotting percentage increase versus concentration for the antitumoral activity of HB6.

The sample denominated HB6 compound presented cytostatic activity for all cell lines from the concentration of 25 µg/mL and cytotoxic activity in the concentration of 250 µg/mL, for HT-29, 786-0, NCI-ADR and K562 cell lines. Furthermore, this sample presented cellular selectivity for HT-29 and 786-0 cell lines. Test data for HB6 is shown in FIG. 7.

Figure 8:
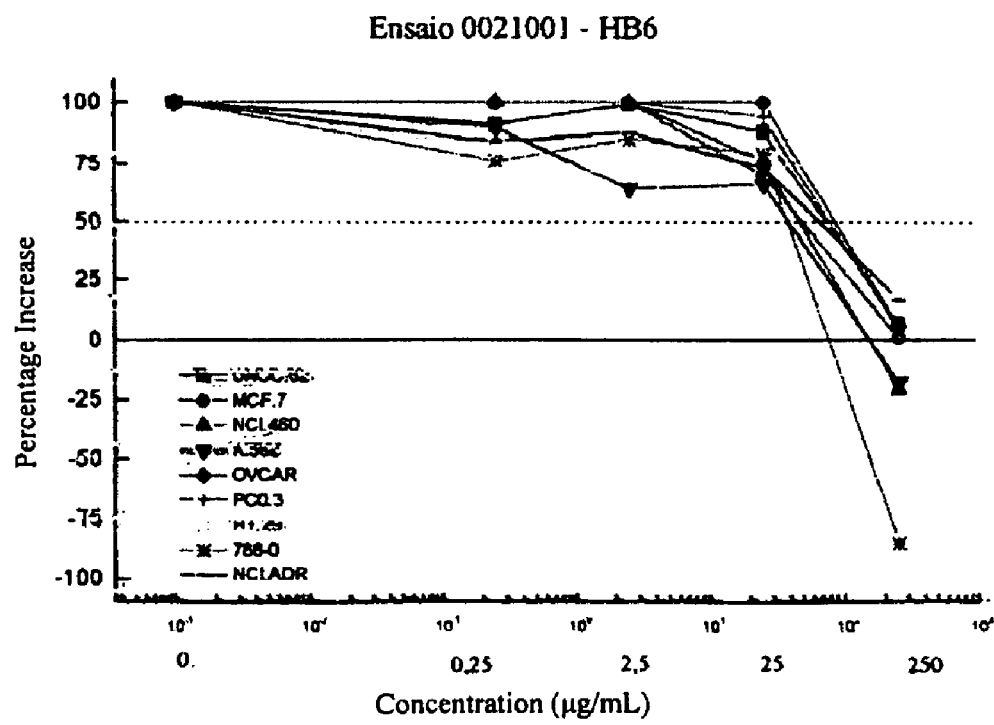
FIG. 8 is a graph plotting percentage increase versus concentration for the activity of HBMI.

The sample denominated HBMI compound presented cytostatic activity for all cell lines from the concentration of 0.25 μg/mL and only presented cytotoxic activity for PC-03 and OVCAR-3 cell lines in the concentration of 250 μg/mL. Test data for HBMI is shown in FIG. 8.

Figure 9:
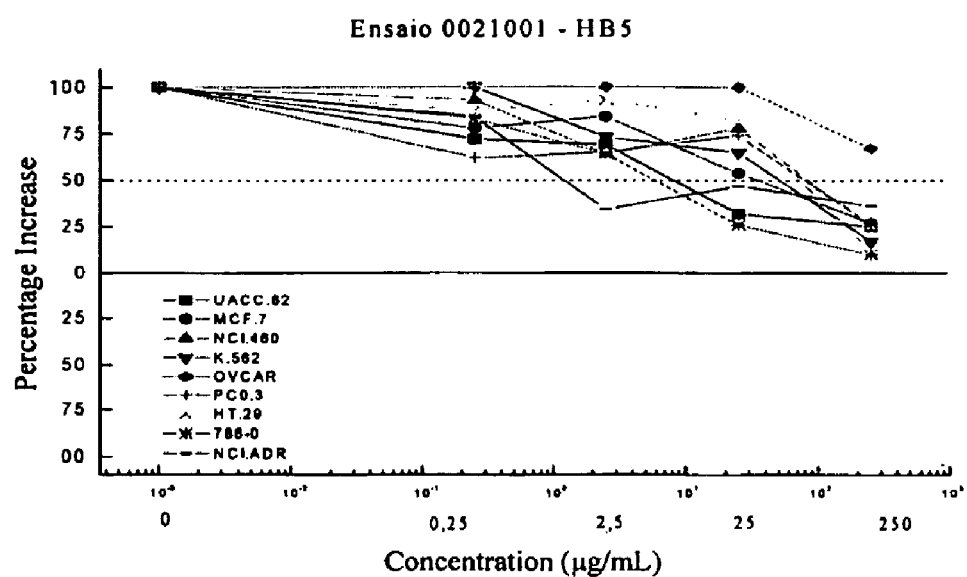
FIG. 9 is a graph plotting percentage increase versus concentration for the activity of HB5.

The sample denominated HB5 compound presented moderate cytostatic activity for all cell lines from the concentration of 0.25 μg/mL and did not present cytotoxic activity for any cell lines in the used concentrations. Test data for HB5 is shown in FIG. 9.

Also a toxicological test with the sample denominated 37 compound (Acute Toxicity I.D$_{50}$, via intraperitoneal). The LD$_{50}$ value, evaluated by linear regression, was equal to 8.54 g/Kg, after 14 days of observation. That means this product can be considered itself, according to Loomis, in Principles of Toxicology, as practically nontoxic (compounds with LD$_{50}$ value between 5.0 and 15 g/Kg are considered practically nontoxic).

Figures 10, 11:
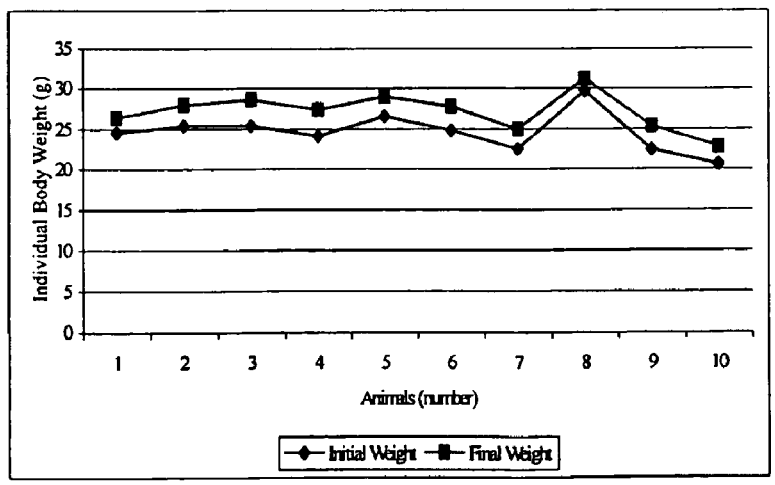
FIG. 10 is a table showing the results of tests of compound 37 on an animal.
FIG. 11 is a graph detailing the evolution of an animal's body weight after receiving administration of 2.5 g of compound 37 per Kg of body weight.

The table shown in FIG. 10 indicates an animal's body weight that received 2.5 g/Kg of animal body weight of the product denominated "37 COMPOUND," administered via intraperitoneal, in the beginning and ending of the acute toxicity test.

The graph of FIG. 11 describes the evolution of the animal's body weight that received 2.5 g/Kg of animal body weight of the product denominated "37 COMPOUND," administered via intraperitoneal, in the beginning and ending of the acute toxicity test.

Figures 12, 13:
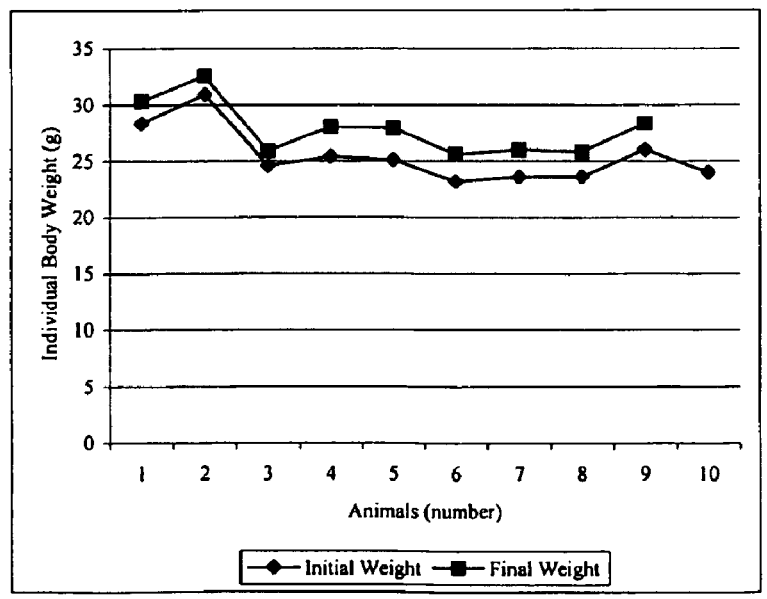
FIG. 12 is a table of data describing change in body weight from tests of 2.5 g of compound 37 per Kg of animal body weight.
FIG. 13 is a graph of the changes in animal body weight resulting from administration of 3.0 g of compound 37 per Kg of animal body weight.

The table of FIG. 12 shows an animal's body weight that received 3.0 g/Kg of animal body weight of the product denominated "37 COMPOUND," administered via intraperitoneal, in the beginning and ending of the acute toxicity test.

The graph of FIG. 13 describes the evolution of the animal's body weight that received 3.0 g/Kg of animal body weight of the product denominated "37 COMPOUND," administered via intraperitoneal, in the beginning and ending of the acute toxicity test.

Figures 14, 15:
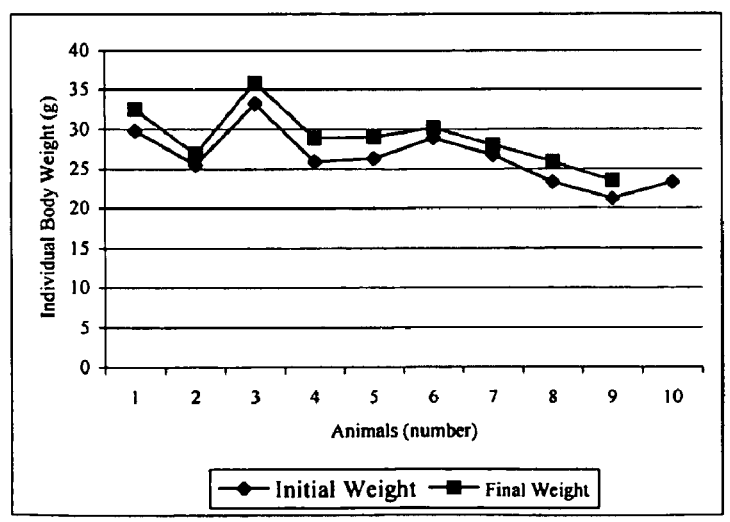
FIG. 14 is a table showing changes in animal body weight resulting from administration of 4.0 g of compound 37 per Kg of animal body weight.
FIG. 15 is a graph of the changes in animal body weight resulting from administration of 4.0 g of compound 37 per Kg of animal body weight.

The table of FIG. 14 shows an animal's body weight that received 4.0 g/Kg of animal body weight of the product denominated "37 COMPOUND," administered via intraperitoneal, in the beginning and ending of the acute toxicity test.

The graph of FIG. 15 shows the evolution of the animal's body weight that received 4.0 g/Kg of animal body weight of the product denominated "37 COMPOUND," administered via intraperitoneal, in the beginning and ending of the acute toxicity test.

Figures 16, 17:
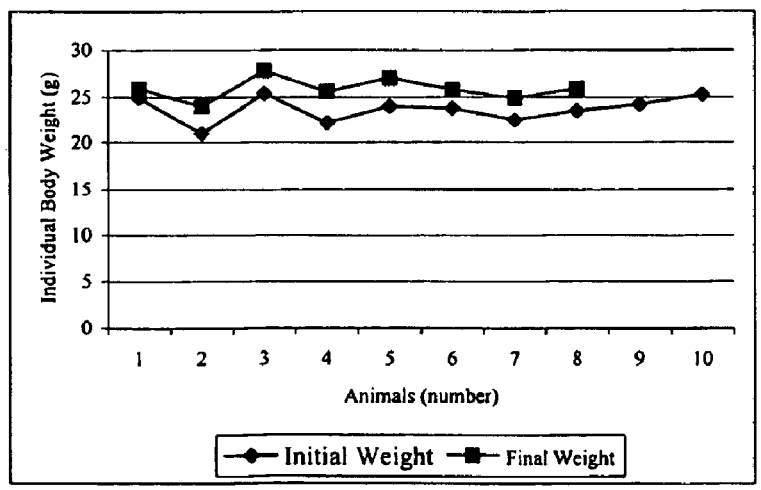
FIG. 16 is a table showing changes in animal body weight resulting from administration of 5.0 g of compound 37 per Kg of animal body weight.
FIG. 17 is a graph of the changes in animal body weight resulting from administration of 5.0 g of compound 37 per Kg of animal body weight.

The table of FIG. 16 shows an animal's body weight that received 5.0 g/Kg of animal body weight of the product denominated "37 COMPOUND," administered via intraperitoneal, in the beginning and ending of the acute toxicity test.

The graph of FIG. 17 shows the evolution of the animal's body weight that received 5.0 g/Kg of animal body weight of the product denominated "37 COMPOUND," administered via intraperitoneal, in the beginning and ending of the acute toxicity test.

Further this invention is illustrated by means of the following examples of execution:

EXAMPLE 1

Preparation of 1,5-bis(4-hydroxy-3-methoxyphenyl)-penta 1,4-dien-3-one. (Method 1)

From vanillin and acetone in a 2:1 molar rate in acid medium, in temperatures that changes between 25 and 60° C., under ultrasonic irradiation conditions in a range from 25 to 40 KHz for a period of 1 to 3 hours further putting the reacted mixture into water/ice until producing the raw product, which dissolves in a solution of sodium hydroxide or potassium hydroxide (between 10-30%) being filtered; the filtrated is treated with hydrochloric acid or sulphuric acid from a concentration between 10-30%, the obtained product being filtered again, finally it is washed with distilled water until obtaining a neutral pH, this operation being repeated until the total purification of the product, not being necessary to perform a new purification of the compound using other procedures such as recrystallization or chromatographic column (the purity was determined by means of the HPLC technique):

Obtained 92% yield of the pure product. Melting point: 155-156° C.

Method of Preparation 2

A mixture formed of vanillin and acetone in a 2:1 molar rate in acid medium laid during 5-8 days, in temperatures that changes between −10 and 40° C., further putting the reacted mixture into water/ice until producing the raw product, which dissolves in a solution of sodium hydroxide or potassium hydroxide (between 10-30%) being filtered: the filtrated is treated with hydrochloric acid or sulphuric acid from a concentration between 10-30%, the obtained product being filtered again, finally it is washed with distilled water until obtaining a neutral pH. This operation is repeated until the total purification of the product, not being necessary to perform a new purification of the compound using other procedures such as recrystallization or chromatographic column (the purity was determined by means of the HPLC technique):

Obtained 89% yield of the pure product, melting point of 155-156° C.

EXAMPLE 2

Preparation of 1,5-bis(3-metoxy-4-acetoxyphenyl) penta-1,4-dien-3-one 1,5-bis(4-hydroxy-3-metoxyphenyl)-penta-1,4-dien-3-one.

It is stirred with an excess of acetic anhydride and sodium acetate. It's heated in a range of temperature between 20 and 110° C. for a period of time between 30 minutes to 3 hours. The obtained product is put into distilled water with ice. The precipitate product is recrystallized with hot ethanol. Yield: 58%. Melting point: 150° C.

EXAMPLE 3

Preparation of 1,5-Bis[3-metoxy-4-(3-methyl-but-2-eniloxy)phenyl]penta-1,4-dien-3-one.

A mixture formed of 1,5-bis(4-hydroxy-3-metoxyphenyl)-penta-1,4-dien-3-one (2 mmol) in 10 mL of dimethylformamide and potassium carbonate (6 mmol) is stirred in a range of temperature between 20-50° C. during a period of time from 20 to 60 minutes in inert atmosphere (argon or nitrogen). After that, 3 mmol of 3-methyl-but-2-enyl bromide with constant stirring. Further, the stir is kept for another period of 5-8 hours with a stream of inert gas pouring all the mixture content into water with ice. It's extracted with chloroform in three occasions with approximately 3 mL of this solvent. The organic phase is washed with a solution of NaRSO$_4$ and then with distilled water. The chloroform phase is dried with sodium sulfate anhydrous. After that, the solvent is filtered and rotoevaporated. The purification of the product is performed utilizing a chromatographic column filled with silica gel and using a mixture formed of toluene/ethyl acetate or n-Hexane/ethyl acetate as elution solvents in an appropriate rate. Yield: 53% of the oil liquid substance.

EXAMPLE 4

Preparation of
1,5-Bis(3,4-dimetoxyphenyl)-penta-1,4-dien-3-one

Method 1

The mixture of 3,4-dimethoxy-benzaldehyd and acetone in equimolecular rate condition in presence of hydrochloric acid was submitted to a ultrasonic bath in the frequence from 25 to 40 KHz between 10-60 minutes in a range of temperature between 25-60° C. Further the obtained product is put into distilled water and ice, filtering the precipitate and washing it with distilled water. The aqueous phase is extracted with chloroform and washing the chloroform phase with distillated water and then the chloroform phase is dried with sodium sulfate anhydrous, filtered and rotoevaporated. Yield: 87%.

Method 2

1,5-bis(4-hydroxy-3-metoxyphenyl)-penta-1,4-dien-3-one is stirred with an excess of dimethyl sulfate or methyl iodide in alkaline medium (KOH or NaOH), stirring it in a range of temperature between 25-50° C. during a period of time that varies between 5-24 hours. The formed mixture is put into cold water, filtering the formed precipitate, neutralizing it with HCl. Further, it is washed with water until neutral pH. The after purification of the product was not necessary. Yield: 85%.

EXAMPLE 5

Preparation of 1,5-Bis(3,4-dimetoxyphenyl)-penta-1,
4-dien-3-ylidenmalonitrile

In a mixture formed of 1,5-Bis(3,4-dimethoxyphenyl)-penta-1,4-dien-3-one and malononitrile in equivmolecular rate condition, ammonium acetate, acetic acid and toluene are added following Cope's variant, heating in reflux for a period of time between 5-16 hours or following Knoevenagel's third variant using piperidine as catalyzer. The obtained product is put into distillated water and ice, filtering the precipitate and extracting the aqueous phase with chloroform and washing the chloroform phase with distillated water. Further, the chloroform phase is dried with sodium sulfate anhydrous, filtered and rotoevaporated. Yield: 76%. Melting point: 216° C.

Methodology utilized to perform the antitumoral tests:

REPORT OF THE ANIPROLIFERATE TEST IN TUMORAL HUMAN CELLS WITH THE SULFORRODAMINA B ESSAY

Cells

The cell lines used in the essays, described in Table 1, were maintained in recipients of 25 cm$^2$ (Nunc®), with 5 mL of culture medium RPMI 1640 supplemented with 5% bovine fetal serum (RPMI/SFB), at 37° C. in atmosphere of 5% of CO$_2$ and 100% of humidity.

TABLE 1

Cellular lineages used in the assessment essays of the antiproliferate activity

| Cellular Type | Code |
|---|---|
| Lung | NCI460 |
| Mama | MCF-7 |
|  | NCI ADR* |
| Melanoma | UACC-62 |
| Colon | HT 29 |
| Renal | 786-0 |
| Ovary | OVCAR-3 |
| Prostate | PC-3 |
| Leukemia | K-562 |

*cell line that expresses the phenotype of resistance against multiple drugs.

All of the procedures described below were performed under sterile conditions (Laminar Flux Veco®, Class IIB2).

Experimental procedure 100 mL of cells in medium RPMI/SFB with 50 μg/mL of Gentamicin were inoculated in its respective densities of inoculation, in plates of 96 compartments and incubated for 24 hours at 37° C. in atmosphere of 5% of CO$_2$ and 100% of humidity.

After 24 hours, 100 mL of the test substance were added in the following concentrations of 250; 25; 2.5; 0.2 μg/mL diluted in RPMI/SFB/gentamicin. In this moment, the reading of one plate was performed for the determination of the T0 (cell control in the moment of adding the samples). The other plates were incubated for 48 hours. After this period, the experiment was paused by adding the trichlorine acetic acid to further determine the protein content by means of colorimetric essay with the sulforrodamina B.

Dilution of the samples

The stocked solutions were developed by diluting the samples in dimethyl sulfoxide (DMSO) in the concentration of 0.1 g/mL. That solution was diluted by 400 times in RPMI/SFB/gentamicina to be added in the plates of 96 compartments being obtained to the ideal concentration of DMSO (Skehan e cols. 1990).

Essay of the Sulforrodamina B (SRB)

At the end of the test, the plates of 96 compartments were centrifuged for 3 minutes at 2000 rpm, and they were fixed with 50 μL of a solution at 50% of trichloroacetic acid (TCA) at 4° C. To complete the cellular fixation, the plates were incubated for 1 hour at 4° C.

The plates were submitted to four consecutive washes with distilled water to remove the residues of TCA, medium, SFB and secondary metabolic and maintained at room temperature until completely dry.

A coloration was performed by the adding of 50 μL SRB at 0,4% (weight/volume) diluted in acetic acid at 1%, and maintained at 4° C. for 30 minutes. Further, they were washed by 4 consecutive times with a solution of acetic acid 1%. The residue of the washing of the solution was removed and the plates were dried again at room temperature. The colorant linked to the cellular protein was diluted with a solution of Trizma Base (Sigma®) in concentration of 10 ∞M and pH 10.5 for 5 minutes in ultrasonic bath. The spectrophotometric of absorbancy reading was performed in 560 nm in a micro plates lector (Labsystems Multiskan® MCC/340).

Analysis of the results

The absorbancy averages were assessed having discounted its respective nulls and by means of the formula shown below was determined the growth inhibition (IC) of each tested sample.

T>C, the drug did not stimulate the growth, it does not present IG.

IF T≧T0 but <C, the drug was cyostatic and the formula used is 100×[(T-To)/(C-T0)].

If T<T0, the drug was cytotoxic and the formula used is 100×[(T-T0)/(C-T0)].

Considering that T is the absorbency average of the treated cell, C is the cell control and T0 is the cell control in the addition day.

The obtained result was subtracted from 100% so obtaining the percentage of growth inhibition. The samples were considered actives since they presented growth inhibition-dependent dose higher than 50% and selective lineage, that is, the preferential activity for only one type of tumoral cell or with cytostatic and/or killed cell effect well distinguished among the cell lines.

All the assays were performed in triplicates so that the presented results make reference to a representative experiment. The standard deflection from the average was always lower than 5%.

Methodology utilized to perform the toxicological tests:

Technique

* Ten albinic Swiss mice are used, of the male gender, weighing approximate 25 g, for each of the treated groups and control.

* Adaptation period: the animals are maintained in the test room for at least seven days before the beginning of the essay.

* The animals are submitted to a fast 12 hours before administering the test substance, done by gavage, at the time the animal's body weight is listed.

* After the administration, the animals are maintained in observation for a minimum period of 14 days.

* The number of dead animals for each one of the doses is listed and the $LD_{50}$ is assessed by Litchfield and Wilcoxon's (1949) method and the animal's body weight is listed at the end of the acute toxicity test.

The invention claimed is:

1. A process for preparing 1,5-bis(4-hydroxy-3-methoxyphenyl)-penta-1,4-dien-3-one, characterized in that it comprises contacting vanillin and acetone under ultrasonic irradiation.

2. A process according to claim 1 characterized in that vanillin and acetone are contacted in a mole ratio of 2:1.

3. A process according to claim 1, characterized in that vanillin and acetone are contacted at temperatures ranging from 25° C. to 60° C.

4. A process according to claim 1, characterized in that the ultrasonic irradiation is in the range of from 25 to 40 KHz.

5. A process according to claim 1, characterized in that vanillin and acetone remain in contact for a period of time ranging from 1 to 3 hours.

6. A process according to claim 1, characterized in that it additionally comprises purifying the purification of 1,5-bis(4-hydroxy-3-methoxyphenyl)-penta-1,4-dien-3-one obtained, mixing the reaction mixture in water/ice until a crude product is obtained, then dissolved in a sodium or potassium hydroxide solution and filtered; the filtrate being treated with an acid selected from the group consisting of hydrochloric acid and sulfuric acid and additional filtration, successive washes with water being then carried out until a neutral pH is achieved.

7. A process according to claim 6, characterized in that the sodium or potassium hydroxide solution is at a concentration between 10% and 30%.

8. A process according to claim 6, characterized in that the hydrochloric or sulfuric acid is at a concentration between 10% and 30%.

9. A process for preparing 1,5-bis(4-hydroxy-3-methoxyphenyl)-penta-1,4-dien-3-one, characterized in that it comprises mixing vanillin and acetone in an acidic under ultrasonic irradiation.

10. A process according to claim 9, characterized in that it additionally comprises purifying 1,5-bis(4-hydroxy-3-methoxyphenyl)-penta-1,4-dien-3-one obtained, mixing the reaction mixture in water/ice until a crude extract is obtained, then dissolved in a sodium or potassium hydroxide solution and filtered; the filtrate being treated with hydrochloric or sulfuric acid and additionally filtered, successive washes with water being carried out until a neutral pH is achieved.

11. A process for preparing 1,5-bis(3-methoxy-4-acethoxy-phenyl)-penta-1,4-dien-3-one, characterized in that it comprises mixing 1,5-bis(4-hydroxy-3-methoxyphenyl)-penta-1,4-dien-3-one, obtained by the process defined in claim 1, and acetic anhydride and sodium acetate.

12. A process of preparing 1,5-bis(3-methoxy-4-acethoxyphenyl)-penta-1,4-dien-3-one, characterized in that it comprises mixing 1,5-bis(4-hydroxy-3-methoxyphenyl)-penta-1,4-dien-3-one, obtained by the process as defined in claim 1, in dimethylformamide and potassium carbonate, and then adding 3-methyl-but-2-enyl bromide.

13. A process according to claim 10, characterized in that 3-methyl-but-2-enyl bromide is added to the mixture of 1,5-bis(4-hydroxy-3-methoxyphenyl)-penta-1,4-dien-3-one.

14. A process according to claim 13, characterized in that it additionally comprises purifying 1,5-bis[3-methoxy-4-(3-methyl-but-2-enyloxy)-phenyl]-penta-1,4-dien-3-one, putting said compound into water with ice, then extracting with chloroform, the washing the organic phase with NaHSO4 and then water; wherein the chloroform phase is dried with anhydrous sodium sulfate, and then the solvent is filtered and rotoevaporated, and then the product is passed through a chromatographic column filled with silica gel.

15. A process of preparing 1,5-bis(3,4-dimethoxy-phenyl)-penta-1,4-dien-3-one, characterized in that it comprises mixing 3,4-dimethoxybenzoaldehyde and acetone in an ultrasound bath.

16. The process according to claim 15, characterized in that 3,4-dimethoxybenzoaldehyde and acetone are mixed in a ratio of 2:1.

17. A process according to claim 15, characterized in that it additionally comprises purifying the 1,5-bis(3-,4-dimethoxyphenyl)-penta-1,4-dien-3-one obtained, putting water with ice, filtering the precipitate, washing it with water, wherein the water phase is extracted with chloroform and the chloroform phase is dried with anhydrous sodium sulfate, filtered and rotoevaporated.

18. A process of preparing 1,5-bis(3-,4-dimethoxy-phenyl)-penta-1,4-dien-3-one, characterized in that is comprises mixing 1,5-bis(4-hydroxy-3-methoxyphenyl)-penta-1,4-dien-3-one obtained, by the processes as defined in claim 1, wherein dimethyl sulfate or methyl iodide.

19. A process according to claim 18, characterized in that it additionally comprises purifying 1,5-bis(3,4-dimethoxyphenyl)-penta-1,4-dien-3-one in ice-cold water, the formed precipitate is filtered, and then neutralized with HCl; then the product is washed with water until a neutral pH is achieved.

20. A process of preparing 1,5-bis(4-hydroxy-3-methoxyphenyl)-penta-1,4-dien-3 yliden-malonitryl, characterized in that it comprises mixing 1,5-bis(4-hydroxy-3-methoxyphenyl)-penta-1,4-dien-3-one, obtained by the process as defined in claim 1 and malonitrile.

21. Pharmaceutical composition for the treatment of cancer, wherein said composition comprises at least one of the compounds obtained by the process defined in claim 1.

22. A therapeutic method for the treatment of cancer, characterized in that one administers a therapeutically effective amount of a compound obtainable by the process as defined in claim 1 to a subject in need of such a treatment.

* * * * *